United States Patent [19]

Kleuskens et al.

[11] 4,409,122

[45] Oct. 11, 1983

[54] CATALYST REACTIVATION

[75] Inventors: Engelina C. Kleuskens, Stein; Johannes G. H. Maessen, Roermond; Theodorus J. van de Mond, Geleen, all of Netherlands

[73] Assignee: Stamicarbon, B.V., Geleen, Netherlands

[21] Appl. No.: 343,362

[22] Filed: Jan. 27, 1982

[30] Foreign Application Priority Data

Jan. 27, 1981 [NL] Netherlands .......................... 8100364

[51] Int. Cl.$^3$ ..................... B01J 27/30; C07C 120/14; C07C 121/32; B01J 27/02
[52] U.S. Cl. .................................. 502/20; 260/465.3; 502/215
[58] Field of Search ........................... 252/411 R, 416; 260/465.3

[56] References Cited

U.S. PATENT DOCUMENTS

| | | | |
|---|---|---|---|
| 3,164,627 | 1/1965 | Minekawa et al. | 260/465.3 |
| 3,236,782 | 2/1966 | Koch | 252/411 R |
| 3,882,159 | 5/1975 | Callahan et al. | 260/465.3 |
| 4,330,429 | 5/1982 | Sasaki et al. | 252/413 |

*Primary Examiner*—P. E. Konopka

[57] ABSTRACT

A process for the reactivation of spent tellurium-containing oxidic catalysts (suitable for oxidation, ammoxidation and/or oxidative dehydrogenation of olefines), wherein a solid particulate tellurium compound especially tellurium oxide compound, is mixed with the spent catalyst to raise the tellurium content thereof to a value of between 90% and 500% of the original catalyst content.

8 Claims, No Drawings

CATALYST REACTIVATION

The invention relates to a process for the reactivation of oxidic catalysts containing tellurium.

It is already known that olefines can be oxidized, ammoxidized or oxidatively dehydrogenated with the aid of an oxidic catalyst, wherein the catalytically active components consist mainly of oxides of one or more of the metals iron and/or antimony, preferably employed together with oxides of one or more of the metals molybdenum, vanadium and tungsten, and one or more oxides of metals such as zinc, tin, cobalt, nickel, magnesium, copper, lanthanum, bismuth, phosphorus and borium, and wherein the catalyst also contains a tellurium oxide as promotor. Such catalysts are described, inter alia, in U.S. Pat. Nos. 3,716,496; 4,049,575; 4,083,804 and Canadian Pat. No. 1,080,203, the disclosures of which are incorporated herein by reference.

The productivity of such catalysts decreases during such use. Productivity is here understood to mean the production of the desired product as a result of both the conversion and the selectivity performance of the catalyst. This observed deterioration in productivity, which is normal for catalysts, can be even more accelerated when the reaction conditions employed are not optimum.

Various processes have been proposed for the reactivation of such iron and/or antimony containing oxide catalysts, for instance, in British patent specification Nos. 2,009,613, 2,010,113 and 2,042,363, the disclosures of which are incorporated herein by reference. However, a disadvantage of these known methods is that the catalyst to be reactivated has to be removed from the reactor and subjected to a series of separate operations.

The process of the invention is to provide a process for the reactivation of the said spent catalyst which preferably is carried out in the simplest way possible.

According to the present invention, a spent oxidic catalyst of the type which is suitable for oxidation, ammoxidation and/or oxidative dehydrogenation of olefins and which contains a tellurium oxide as promotor and which has as active components mainly oxides of antimony and/or iron is reactivated by mixing the spent catalyst with a solid particulate tellurium compound or with a particulate, solid carrier material containing a tellurium compound, in an amount which is sufficient to raise the tellurium content (calculated as metal) of the reactivated catalyst to a value of between 90% and 500% by weight of the tellurium content of the original catalyst.

The applicant has found that a decrease in the productivity of the catalyst is attended by a reduction of its tellurium content. This does not necessarily imply that there is a direct causal connection between these two phenomena. However, applicant has discovered that the productivity, and particularly the selectivity, is again increased by adding a tellurium compound to the spent catalyst.

Generally, the catalyst needs to be reactivated when the productivity has decreased by between 5% and 10% of the original value. The catalyst generally will be reactivated when the tellurium content still is at least 50%, and preferably at least 75%, of the original tellurium content. It is, however, also possible to exhaust the catalyst even further before reactivating it, or, conversely, to reactivate it sooner, if this is more advantageous from an overall plant economic point of view.

The tellurium compound may be mixed with the spent catalyst in the reactor itself, especially when a fluid bed reactor is used, or in a separate mixing unit. The catalyst reactivation can be obtained by applying a heat or calcination treatment to the mixture of spent catalyst and tellurium compound, but preferably the reactivation takes place under reaction conditions in the catalytic reactor.

By preference, the tellurium compound which is mixed with the spent catalyst is tellurium oxide or a compound which is easily converted into a tellurium oxide under the conditions of use or in the process of calcination, i.e., at a temperature between 600° C. and 900° C.

In particular, the use of tellurium oxide is preferred. The advantage of this method is that the added solid tellurium compound can easily be mixed with the catalyst to be reactivated. In the case of those catalysts which are used in fluidized condition, it is possible simply to add the solid tellurium compound to the catalyst bed, without removing the catalyst to be reactivated from the reactor. By employing the added tellurium oxide on a carrier material, the additional advantage is realized that the particles can be processed more easily into a suitable shape and that particles can be prepared which have fluidization properties compatible with the fluidization properties of the catalyst to be regenerated. The tellurium content of such carrier material containing tellurium oxide may vary between 5% and 80% by weight. Optionally, other metal oxides may also be present besides tellurium oxide.

That the addition of tellurium oxide, on a carrier or not, produces such an effect is remarkable, because under the reaction conditions tellurium oxide is hardly volatile and therefore migration of the tellurium in one form or another is not to be expected.

In general, an amount of tellurium compound is added such that the tellurium content (calculated as metal) of the reactivated catalyst is between 90% and 500% of the original tellurium content, by weight. Advantageously, such an amount is added that the tellurium content is between 90% and 200%, and more in particular between 95% and 150%, of the original tellurium content. Reactivated catalyst is here understood to include the mixture of spent catalyst and the added tellurium oxide, on a carrier or not. The reactivated catalyst substantially behaves as a fresh catalyst and in particular retains its restored activity to the same extend as a fresh catalyst retains its initial activity.

The process generally can be applied to tellurium-containing oxidic catalysts that are used for oxidation or ammoxidation or oxidative dehydrogenation of olefines.

Examples of catalysts that are suitable especially for the oxidation and ammoxidation of olefines are the oxidic catalysts on an iron-antimony oxide basis which have as essential components iron, antimony, and tellurium as a promotor, and one or more of the elements within, molybdenum and tungsten, and optionally one or more of the elements copper, magnesium, zinc, lanthanum, cerium, aluminum, chromium, manganese, cobalt, nickel, bismuth, tin phosphorus and borium. The overall atomic composition of these catalysts, apart from the carrier material, is $Fe_{10}Sb_aTe_bMe_cX_dO_e$, wherein Me is at least one of the elements copper, magnesium, zinc, lanthanum, cerium, aluminum, chromium, manganese, cobalt, nickel, bismuth, tin, phosphorus and borium, and the number values of a, b, c and d are respectively 50-80, 0.1-10, 0.01-10 and 0-20, while e represents the number of oxygen atoms corresponding with an oxydic structure.

The invention will be elucidated and further understood on the basis of the following non-limiting Examples.

EXAMPLE I

Propylene was converted into acrylonitrile by passing a gaseous mixture of propylene, ammonia and air through a fluidized catalyst bed at a pressure of 1 atm. and a temperature of 430° C. The gaseous mixture consisted of 7.7 vol.% of propylene, 8.36 vol.% of ammonia and 17.54 vol.% of oxygen, the remainder being nitrogen. The gaseous mixture was passed through at a linear rate of 1.79 cm/sec. The total amount of gas passed through per hour was 15.71.

In test No. 1 the reactor contained 40 g of a catalyst substantially in accordance with example 4 of British Patent specification No. 2009613. The productivity of this catalyst, initially amounting to about 74.5%, had decreased after 6 months of use in a commercial acrylonitril production until operating at a temperature of 440°-445° C. with a reaction mixture close to that stated above. The tellurium content (calculated as metal) of this catalyst was then decreased to about 83%, by weight of that contained in the fresh catalyst.

The said "spent catalyst" was thereafter used but only after having introduced in the reactor 0.28 tellurium dioxide per 40 g of the above-mentioned catalyst while the same continues to be fluidized in the reactor, under reaction conditions. Using a gas chromatograph, the composition of the reaction gas was determined at the reactor outlet, at the stated time intervals after $TeO_2$ introduction listed under "tests" 2 through 6, so that the propylene conversion and the selectivity towards acrylonitrile, and the overall productivity could be calculated. Otherwise, the reaction conditions were unchanged. The results are tabulated below.

| Test No. | 1 | 2 | 3 | 4 | 5 | 6 |
|---|---|---|---|---|---|---|
| Time after $TeO_2$ introduction, hours | — | ½ | 2 | 3 | 4 | 24 |
| Propylene conversion, % | 95.4 | 95.0 | 95.5 | 95.5 | 95.7 | 95.9 |
| Selectivity towards acrylonitrile, % | 74.3 | 77.1 | 76.8 | 77.2 | 77.2 | 77.6 |
| Productivity | 70.9 | 73.3 | 73.4 | 73.8 | 73.9 | 74.5 |

It will be seen from this Table that within ½ hour from the addition of the tellurium oxide (only 0.5% by weight of the "spent catalyst") the productivity had increased from 70.9 to 73.3%, largely from the rapid improvement in selectivity, and that over the 24 hour period both the conversion and selectivity continued to improve with consequent improvements in productivity.

The reactivated catalyst substantially behaves as the fresh catalyst in respect of its ageing properties and in particular retains a productivity of about 70,8% after 6 months use under commercial conditions.

What is claimed is:

1. A process for the reactivation of a spent oxidic catalyst, which is suitable for oxidation, ammoxidation and/or oxidative dehydrogenation of olefines, which catalyst contains a tellurium oxide and as principal active components antimony and/or iron oxides, said process consisting essentially in mixing the spent catalyst with a solid particulate tellurium compound or with a particulate, solid carrier material containing a tellurium compound, in an amount sufficient to raise the tellurium content, calculated as metal, of the reactivated catalyst to a value between 90% and 500% by weight of the tellurium content of the original, fresh catalyst.

2. Process according to claim 1, wherein said oxidic catalyst is on a solid particulate carrier material.

3. Process according to claim 1, wherein said value is from 90% to 200%.

4. Process according to claim 3, wherein said value is from 95% to 150%.

5. Process according to any one of claims 1, 2, 3 or 4, wherein said tellurium compound is tellurium oxide or a tellurium compound that is converted into a tellurium oxide under the conditions of use or by calcination at a temperature between 600° C. and 900° C.

6. Process according to any one of claims 1, 2, 3 or 4, wherein said tellurium compound is tellurium oxide.

7. Process according to any one of claims 1, 2, 3 or 4, wherein the catalyst is reactivated by mixing the spent catalyst with tellurium oxide on a solid particulate carrier material.

8. Process according to any one of claims 1, 2, 3 or 4, wherein said oxidic catalyst has the formula $Fe_{10}Sb_aTe_bMe_cX_dO_e$ where Me is at least one of the elements copper, magnesium, zinc, bismuth, tin, phosphorus and borium, a is 5-80, b is 0.1-10, c is 0.01-10, d is 0 to 20 and e is the number of oxygen atoms required to satisfy the resulting oxidic structure.

* * * * *